United States Patent [19]

Duranleau

[11] 4,421,863
[45] Dec. 20, 1983

[54] PROCESS FOR PREPARING LOW MOLECULAR WEIGHT OXYGENATED COMPOUNDS FROM SYNGAS USING A NOVEL CATALYST SYSTEM

[75] Inventor: Roger G. Duranleau, Georgetown, Tex.

[73] Assignee: Texaco Inc., White Plains, N.Y.

[21] Appl. No.: 344,276

[22] Filed: Feb. 1, 1982

[51] Int. Cl.³ .............................................. C07C 27/06
[52] U.S. Cl. ................................................... 518/701
[58] Field of Search ................................ 518/701, 716

[56] References Cited

U.S. PATENT DOCUMENTS

| | | | |
|---|---|---|---|
| 3,833,634 | 9/1974 | Pruett et al. | 518/701 |
| 4,190,598 | 2/1980 | Kaplan | 518/701 |
| 4,197,253 | 4/1980 | Kaplan | 518/701 |

FOREIGN PATENT DOCUMENTS 1565979  4/1980  United Kingdom ................ 518/700

*Primary Examiner*—Howard T. Mars
*Attorney, Agent, or Firm*—Carl G. Ries; Jack H. Park; Walter D. Hunter

[57] ABSTRACT

Low molecular weight oxygenated compounds, and particularly ethylene glycol and methanol, are prepared from syngas in improved yields by contacting a mixture of carbon monoxide and hydrogen with a catalyst system comprising a rhodium-containing compound, an organic ligand and a special cationic polynuclear aromatic compound possessing a nitrogen atom at a ring fusion position, dissolved in a suitable solvent, and heating the resulting reaction mixture at a temperature of at least 150° C. and a pressure of at least 500 psi for sufficient time to produce the desired low molecular weight oxygenated compounds, and then recovering the same from the reaction mixture.

19 Claims, No Drawings

PROCESS FOR PREPARING LOW MOLECULAR WEIGHT OXYGENATED COMPOUNDS FROM SYNGAS USING A NOVEL CATALYST SYSTEM

BACKGROUND OF THE INVENTION

1. Field of the Invention

This invention relates to a new process for preparing low molecular weight oxygenated compounds. More particularly, the invention relates to an improved process for preparing low molecular weight oxygenated compounds, and particularly ethylene glycol and methanol, from syngas using a novel catalyst system.

Specifically, the invention provides a new and improved process for preparing low molecular weight oxygenated compounds, and particularly ethylene glycol and methanol, from syngas in improved yields, which process comprises contacting a mixture of carbon monoxide and hydrogen with a catalyst system comprising a rhodium-containing compound, an organic ligand and a special cationic fused ring polynuclear aromatic compound having a nitrogen atom at a ring fusion position, dissolved in a suitable solvent, and heating the resulting mixture at a temperature of at least 150° C. and a pressure of at least 500 psi for sufficient time to produce the desired low molecular weight oxygenated compounds, and then recovering the same from the reaction mixture.

2. Prior Art

Low molecular weight oxygenated compounds, such as ethylene glycol and methanol, are chemicals which have found wide use in industry. Ethylene glycol, for example, is used in preparation of plasticizers for vinyl polymers and as a component in polyester fibers and antifreeze formulations. Low molecular weight alcohols, such as methanol, find use as solvents and in the production of esters, such as ethyl esters, which can subsequently be used to produce ethylene. In view of these many uses, there is a need to find new and more economical methods for preparing these chemicals.

On proposed mode of making ethylene glycol involves the reaction of carbon monoxide with hydrogen in the presence of variously proposed catalyst systems. In general, the mixture of carbon monoxide and hydrogen, commonly known as synthesis gas or syngas, is reacted at elevated temperatures and pressures in the presence of the proposed catalyst. U.S. Pat. No. 2,636,046 discloses the production of ethylene glycol from syngas using a cobalt catalyst. Belgium Patent No. 793,086 and U.S. Pat. No. 3,940,432 describe the cosynthesis of ethylene glycol and methanol from mixtures of carbon monoxide and hydrogen using a complex rhodium catalyst. U.S. Pat. No. 3,833,634 describes the use of various other metals as catalysts but indicates that only rhodium and cobalt are effective in producing ethylene glycol. Other patents disclosing catalyst systems for converting syngas into polyhydric alcohols are listed in U.S. Pat. No. 4,162,261.

Many of these proposed processes are limited, however, by the nature and activity of the catalyst systems. For example, many of the catalyst systems have poor selectivity as to the production of the desired polyhydric alcohols, or are based on very expensive components. Other catalyst systems have poor solubility in conventional reaction solvents, or have limited solubility with a plating out of the expensive components, such as rhodium, during the reaction.

It is the object of the invention, therefore, to provide an improved process for preparing low molecular weight oxygenated compounds, and particularly ethylene glycol and methanol. It is a further object to provide a new process for preparing ethylene glycol and methanol from syngas using a new catalyst system. It is a further object to provide a new process for preparing ethylene glycol and methanol from syngas which gives improved yields and greater selectivity. It is a further object to provide a new catalyst system for producing ethylene glycol and methanol from syngas which has improved solubility in conventional reaction solvents. It is a further object to provide a new process for preparing ethylene glycol and methanol from syngas which avoids the plating out of expensive components, such as rhodium, during the reaction. Other objects and advantages of the invention will appear hereinafter.

SUMMARY OF THE INVENTION

It has now been discovered that these and other objects may be accomplished by the process of the invention comprising contacting a mixture of carbon monoxide and hydrogen with a catalyst system comprising a rhodium-containing compound, an organic ligand and a special cationic fused ring polynuclear aromatic compound having a nitrogen atom at a ring fusion position, dissolved in a suitable solvent, and heating the resulting mixture at a temperature of at least 150° C. and a pressure of at least 500 psi for sufficient time to produce the desired low molecular weight oxygenated compound, and then recovering the same from the reaction mixture. It was surprising to find that by the use of the above-noted new catalyst systems one can obtain greater selectivity in the formation of the desired ethylene glycol, and can obtain the said glycol in higher yields than obtainable heretofore with many of the related processes. In addition, the new catalyst system has improved solubility in many of the convention solvents and thus more easily utilized in the reaction mixture. Further, the new process surprisingly avoids the plating out of the expensive catalyst components, such as rhodium, during the reaction and during the product recovery. Further advantage is found in the fact that the process can be operated at moderate temperatures and pressures and avoids the use of extreme conditions required in many of the prior known processes.

The process of the invention as far as the formation of the desired ethylene glycol is concerned may be represented by the following equation:

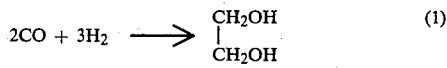

Typical yields of ethylene glycol based on liquid weight changed range from about 0.5 to about 20.0%.

DETAILED DESCRIPTION OF THE INVENTION

In the operation of the process of the invention, the low molecular weight oxygenated compounds, and particularly ethylene glycol and methanol, are prepared concurrently from a synthesis gas mixture of carbon monoxide and hydrogen by a process comprising the following steps:

(1) contacting the said mixture of carbon monoxide and hydrogen with a catalyst comprising a rhodium-containing compound, an organic ligand and a special cationic fused ring polynuclear aromatic compound having a nitrogen atom at a ring fusion position, dissolved in a suitable solvent, (b) Heating the said mixture to a temperature of at least 150° C. and a pressure of at least 500 psi with sufficient carbon monoxide and hydrogen to satisfy the above-noted stoichiometry of the desired ethylene glycol synthesis, until substantial formation of the desired ethylene glycol has been achieved, and, (c) Preferably isolating the said ethylene glycol, monohydric alcohols and other low molecular weight oxygenated products.

In order to present the inventive concept of the present invention in the greatest possible detail, the following supplementary disclosure is submitted. The process of the invention is practiced as follows:

As noted, the new catalyst system used in the process of the invention contains a rhodium-containing compound, an organic ligand and a cationic acridizinium salt. The rhodium-containing compound to be used may be chosen from a wide variety of organic or inorganic compounds, complexes, etc. It is only necessary that the compound actually employed contain the rhodium in any of its ionic states.

The rhodium-containing compound may taken many different forms. For instance, the rhodium may be added to the reaction mixture in an oxide form, as in the case of, for example, rhodium(III) oxide hydrate ($Rh_2O_3.5H_2O$), rhodium(IV) dioxide ($RhO_2$) and rhodium sesquioxide ($Rh_2O_3$). Alternatively, it may be added as the salt of a mineral acid, as in the case of rhodium(III) chloride hydrate, rhodium(III) bromide, rhodium(III) iodide, chlorodiocarbonyl rhodium(I) dimer, anhydrous rhodium(III) chloride and rhodium nitrate, or as the salt of a suitable organic carboxylic acid, for example, rhodium(II) formate, rhodium(II) acetate, rhodium(II) propionate, rhodium(II) butyrate, rhodium(II) valerate, rhodium(III) naphthenate, rhodium(III) acetylacetonate, etc. The rhodium may also be added to the reaction zone as a carbonyl or hydrocarbonyl derivative. Here, suitable examples include tetrarhodium dodecacarbonyl, dirhodium octacarbonyl, hexarhodium hexadecacarbonyl ($Rh_6(CO)_{16}$), rhodium tetracarbonyl salts, and substituted carbonyl species such as rhodium dicarbonyl acetylacetonate.

Preferred rhodium-containing compounds include oxides of rhodium, rhodium salts of a mineral acid, rhodium salts of organic carboxylic acids and rhodium carbonyl or hydrocarbonyl derivatives. Among these, particularly preferred are, rhodium(III) acetylacetonate, rhodium dicarbonyl acetylacetonate, rhodium(II) acetate, rhodium(II) propionate, and hexarhodium hexadecacarbonyl.

Any suitable ligand can be used in the catalyst system of the present invention. Examples of those ligands which form complexes or associations with the rhodium-containing compound include, among others, those which contain at least one Lewis base nitrogen atom and/or at least one Lewis base oxygen atom, as well as those which contain elements of phosphorous, arsenic and antimony, and the like. The only requirement is that they form a suitable electronic or ionic association with the rhodium.

Organic ligands which contain at least one Lewis base nitrogen atom preferably contain carbon, hydrogen and nitrogen atoms. The carbon atoms can be acyclic and/or cyclic such as aliphatic, cycloaliphatic, aromatic (including fused and bridged) carbon atoms, and the like. Preferably, the organic ligands contain from 2 to 20 carbon atoms. The nitrogen atoms can be in the form of imino (—N=), amino, nitrilo, etc. Desirably the Lewis base nitrogen atoms are in the form of imino nitrogen and/or amino nitrogen.

Illustrative examples of the organic nitrogen ligands include, among others, N,N,N',N'-tetramethylethylenediamine, N,N,N',N'-tetraethylethylenediamine, N,N,N',N'-tetraisobutylmethylenediamine, piperazine, N-methylpiperazine, N-ethylpiperazine, 2-methyl-N-methylpiperazine, 2,2'-dipyridyl, purine, 2-aminopyridine, 2-(dimethylamino) pyridine, 1,10-phenanthroline, methyl-substituted 1,10-phenanthroline, piperidine, 2-methylpiperidine, pyridine, triethylamine, benzyltrimethyl ammonium acetate, tri-n-butylamine, dibutylamine, methylamine, dodecylamine, morpholine, aniline, benzylamine, octadecylamine, naphthylamine, cyclohexylamine, and the like, and mixtures thereof.

Organic ligands which contain at least one Lewis base oxygen atom preferably contain carbon, hydrogen and oxygen atoms. The carbon atoms can be acyclic and/or cyclic such as aliphatic, cycloaliphatic, aromatic (including fused and bridged) carbon atoms, and the like. Preferably the ligand contains from 2 to 20 carbon atoms. The oxygen atom can be in the form of groups such as hydroxyl (aliphatic or phenolic), carboxyl, etc., the oxygen atom in the hydroxyl group and carboxyl group, etc. being the Lewis base oxygen atom. Such ligands may, of course, contain other atoms and/or groups, such as alkyl, cycloalkyl, aryl, chloro, thiaalkyl, thiaalkylsilyl, and the like.

Illustrative examples of the organic ligands containing oxygen include, among others, glycolic acid, methoxyacetic acid, ethoxyacetic acid, diglycolic acid, thiodiglycolic acid, diethyl ether, tetrahydrofuran, dioxane, tetrahydropyran, pyrocatechol, citric acid, 2-methoxyethanol, 2-n-butanol, 1,2,3-trihydroxybenzene, 2,3-dihydroxynaphthalene, cyclohexane-1,2-diol, oxetane, 1,2-dimethoxybenzene, 1,2-dimethoxybenzene, 1-4 dimethoxybenzene, methyl acetate, ethanol, 1,2-dipropoxyethane, hexane-2,4-dione, 1-phenylbutane-1,3-dione, 3-methylpentane-2,4-dione, the mono- and dialkyl ethers of propylene glycol, of diethylene glycol of dipropylene glycol, and the like, and mixtures thereof.

Illustrative examples of those compounds containing both oxygen and nitrogen include, among others, ethanolamine, diethanolamine, isopropanolamine, N,N-dimethylglycine, iminodiacetic acid, N-methyliminodiacetic acid, N-methyldiethanolamine, 2-hydroxypyridine, picolinic acid, methyl-substituted picolinic acid, nitrotriacetic acid, 2,5-dicarboxypiperazine, N(2-hydroxyethyl)iminodiacetic acid, ethylenediaminetetracetic acid, 2,6-dicarboxypyridine, 8-hydroxyquinoline, cyclohexane-1,2-diamine-N,N,N',N'-tetracetic acid, the tetramethyl ester of ethylenediaminetetracetic acid, and the like, and mixtures thereof.

Coming under special consideration are the Group VB tertiary donor ligands, preferably containing nitrogen, phosphorous, arsenic and antimony. Illustrative examples of this group include, among others, triphenylphosphine, tributylphosphine, triphenylphosphite, triethylphosphite, trimethylarsin, triphenylarsine, tricyclohexylphosphine, dimethylphenylphosphine, trioctylphosphine, triphenylstilbine, trimethylamine, triethylamine, tripropylamine, pyridine, 2,2'-dipyridyl, N,N'dimethylpiperazine, 1,8-bis(dimethylamino)naphthalene and N,N-dimethylaniline.

The above-noted ligands can be combined with the rhodium-containing compound prior to addition to the reaction mixture, or the two components can be added separately. In general, it is preferred to add the two components separately to the reaction mixture.

The promoters to be used in the catalyst system of the present invention comprise cationic fused ring polynuclear aromatic compounds having a quaternary nitrogen atom at an aromatic ring fusion position, but never have a nitrogen to nitrogen linkage, i.e. never a >N—< linkage. This makes the cationic charge an essential part of the molecular aromaticity. The aromaticity, in turn, stabilizes and disperses the charge which is the desired function of the promoter. Such compounds may have 2 or more fused aromatic rings and at least one quaternary nitrogen atom at a ring fusion position, but as noted above, never a nitrogen to nitrogen linkage. The rings may be further substituted with non-interfering substituents, such as alkyl, alkenyl, cycloalkyl, cycloalkenyl, aryl, alkaryl, ether groups, ester groups, and the like. The anionic portion of the salt molecule may be any suitable anionic group including, among others, halides, acetates, benzoates, and the like.

Examples of such promoters include, among others, compounds such as the phenanthradaziniums

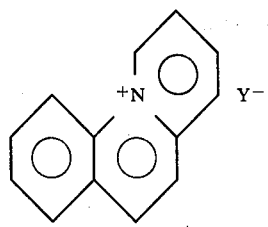

naphthaziniums which are sometimes termed dehydroquinolaziniums

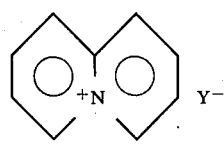

acridaziniums

wherein Y is any suitable anionic group, and derivatives thereof, such as compounds of the formula

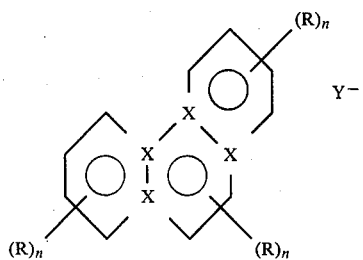

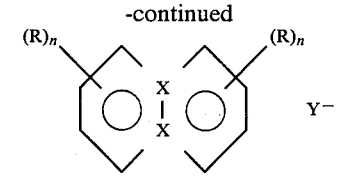

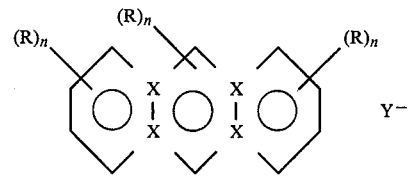

wherein at least one X is a quaternary nitrogen and the other Xs are carbon atoms (if there is more than one X they should not be in a nitrogen-to-nitrogen linkage), Y is an anionic group, R is a monovalent substituent, and preferably hydrogen, a hydrocarbyl or hydrocarbyloxy group, and n is an integer, preferably 1 to 6. Examples of these compounds include, among others, phenanthradizinium chloride, naphthazinium bromide, 9-methylacradizinium bromide, 9-methoxyacridazinium iodide, 9-butylphenanthradazinium acetate, 7,9-dimethoxyacridazinium bromide, 7,9-dimethoxyacridazinium bromide, 8-methoxynaphthazinium iodide, 8,9-dibutylnaphthazinium benzoate, 9,10-dihexylnaphthazinium butyrate, 8-chloroacridazinium bromide, *,7,12-tributylacridazinium toluate, and the like.

Coming under special consideration are those compounds of the formula

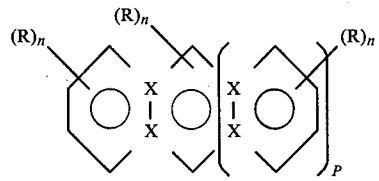

where X,Y,R and n are as described above, and p is an integer from 1 to 6. Also of special consideration are the acridizinium salts and preferably the halides and the alkanoates salts.

A method for preparing many of the above-noted salts may be found in the Journal of the American Chemical Society, Vol. 77, page 4812, (1955).

The amount of the rhodium-containing compound to be used in the process may vary over a wide range. The process is conducted in the presence of a catalytically effective quantity of the rhodium-containing compound which gives the desired product in a reasonable yield. The reaction proceeds when employing as little as about $1 \times 10^{-6}$ weight percent, and even lesser amounts of the rhodium-containing compound. The upper concentration is dictated by a variety of factors including catalyst cost, partial pressures of carbon monoxide and hydrogen, operating temperatures, etc. A rhodium-containing compound concentration of from about $1 \times 10^{-5}$ to about 10 weight percent, based on total weight of the reaction mixture is generally desirable in the practice of the invention.

The amount of the organic ligand to be used in the process of the invention may vary over a wide range depending upon the type of complex to be formed. For example, the amount may vary from that stoichiometric amount need to form the required complex with the rhodium up to 10 or more times the molar amount needed for the formation of such complexes. Preferably, the amount of ligand utilized varies from about 0.5 to about 6.0 moles of ligand per mole of rhodium (contained in the rhodium-containing compound). Ratios outside this range can be employed especially when it is desirable to use diluent quantities of the organic ligand.

A method for determining the optimum amount of the ligand to use with the rhodium catalyst is disclosed in Britain Patent No. 1,565,979 and such pertinent portions of that disclosure is incorporated herin by reference.

The acridizinium salt promoters are generally added to the reaction mixture in amounts varying from about 0.3 to about 2.0 moles for every five atoms of rhodium present. Preferably the salt is added in amounts varying from about 0.8 mol to about 1.6 moles per 5 atoms of the rhodium contained in the catalyst system.

Solvents can and preferably are employed in the process of the invention. As noted above, one of the advantages of the present invention is that the new catalysts are readily soluble in the conventional solvents used in this type of reaction. In general, the preferred solvents are those which are not of the ligand type but which act chiefly to fluidize the catalysts. They are thus preferably substantially inert under the reaction conditions, relatively non-polar and preferably have a boiling point greater than that of of the ethylene glycol and other oxygen-containing reaction products so that recovery of the solvent by distillation is facilitated.

Suitable solvents include the liquid hydrocarbons, which can be aliphatic, cycloaliphatic or aromatic, such as, for example, benzene, toluene, xylene, heptane, dodecane, cyclohexane, and the like, and mixtures thereof. Other suitable solvents include the ethers which may be cyclic, acyclic, and heterocyclic materials. Examples of these include isopropyl propyl ether, diethylene glycol dibutyl ether, tetraethylene glycol dimethyl ether, tetraethylene glycol dibutyl ether, diphenyl ether, heptyl phenyl ether, anisole, tetrahydrofuran, 1,4-dioxane and the like, and mixtures thereof. Coming under special consideration are the dialkyl ethers of alkylene glycols and the dialkyl ethers of poly(alkylene glycols).

Less preferred solvents include the alcohols, such as cyclohexanol, 2-hexanol, 2-octanol, neopentanol, and the like. Also less preferred are the liquid esters which may be aliphatic, cycloaliphatic or aromatic carboxylic acid esters, such as methyl benzoate, butyl cyclohexanoate, dimethyl adipate, dibutyl succinate, and the like, and mixtures thereof.

The amount of the solvent employed may vary as desired. In general, it is desired to use sufficient solvent to fluidize the catalyst system. In general, this may vary from about 0.3 mol to 100 mol per mol of rhodium.

The temperature range which can be employed in the process of the invention may vary over a considerable range depending upon experimental factors, including the choice of catalyst, pressure and other variables. A preferred range of operability is from about 170° C. to about 350° C. when superatmospheric pressures of syngas are employed. A narrower range of about 170° C. to 290° C. represents a particularly preferred temperature range.

The pressure employed may also vary over a considerable range, but in most cases is at least above 500 psig. A preferred operating range varies from about 1000 psig to about 15,000 psig, although pressures above 15,000 psig also provide useful yields of the desired product. The pressures referred to herein represent the total pressure generated by all the reactants, although they are substantially due to the carbon monoxide and hydrogen fractions.

The relative amounts of carbon monoxide and hydrogen which can be initially present in the syngas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon, and the like, or they may include gases that may, or may not, undergo reaction under carbon monoxide hydrogenation conditions, such as carbon dioxide, hydrocarbons, such as methane, ethane, propane, and the like, ethers, such as dimethyl ether, methylethyl ether and diethyl ether, alkanols, such as methanol, and the like.

In all these synthesis in order to achieve a high degree of selectivity the amount of carbon monoxide and hydrogen present in the reaction mixture should be sufficient to at least satisfy the stoichiometry of the desired formation of ethylene glycol as shown in equation (1) above. Excess carbon monoxide and/or hydrogen over the stoichiometric amount may be present, if desired.

The desired product of the reaction, ethylene glycol, will be formed in significant quantities generally varying from about 2% to 20% by weight. This represents weight of material charged in the sufficient amount of time. Also formed will be significant amounts of the lower monohydric alcohols, such as methanol and ethanol. Other derivatives such as acetic acid and ethylene glycol ethers, may also be formed in very minor amounts. The ethylene glycol, monohydric alcohols and other by-products can be recovered from the reaction mixture by conventional means, e.g. fractional distillation in vacuo.

The novel process of the invention can be conducted in a batch, semi-continuous or continuous manner. The process is preferably conducted in a batch manner. The catalyst can be initially introduced into the reaction zone batchwise, or it may be continuously or intermittently introduced into such a zone during the course of the synthesis reaction. Operating conditions can be adjusted to optimize the formation of the desired ethylene glycol product, and said material may be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures: viz, gas-liquid phase chromatography (glc), infrared (ir) mass spectrometry, nuclear magnetic resonance (nmr) and elemental analyses, or a combination of these techniques. Analyses have, for the most part, been by parts by weight; all temperatures are in degrees centigrade and all pressures in pounds per square inch (psi).

To illustrate the process of the invention, the following examples are given. It is to be understood, however, that the examples are given in the way of illustration and are not to be regarded as limiting the invention in any way.

EXAMPLE I

This example illustrates the preparation of ethylene glycol and methanol using rhodium(II) acetylacetonate with 2-hydroxypridine as the ligand and acridizinium bromide as the promoter and tetraethylene glycol dimethyl ether as solvent.

In to a glass liner, designed to fit into a stainless steel rocking autoclave capable of withstanding 15,000 psig were added the following components: 0.300 grams (0.75 mmole) of rhodium(III) acetylacetonate, 0.2375 grams (2.5 mmoles) of 2-hydroxypyridine, 0.0327 grams (0.125 mmole) of acridizinium bromide and 19.0 grams (0.082 mole) of tetraethylene glycol dimethyl ether solvent. The resulting suspension was placed in the autoclave, sealed and flushed with 1/1:CO/H$_2$, then pressurized to 3000 psig with this gas mixture while rocking at room temperature. The temperature was then gradually increased to 220° C. and stabilized. The system was pressurized to 8500 psig and repressured periodically over a four hour span at it dropped to 8120 psig. The system was dismantled after cooling and relieving the pressure. An off gas sample was collected. A weight gain of 0.4332 gram was observed by measuring the liquid products. The liquid products were found to contain 0.691% ethylene glycol, 0.694% methanol along with traces of methyl formate, ethanol, a hydroxypyridine and 2,4-pentanedione and 95.8% tetraethylene glycol dimethyl ether, by G.C. analysis. The recovered solution was not perfectly clear but no plating of rhodium or precipitated material was observed.

EXAMPLE II

A reference run was conducted in triethylene glycol dimethyl ether using the same equipment and ingredients as Example I without the acridizinium bromide promoter. No liquid weight gain was observed and the liquid portion of the liner had 0.69% ethylene glycol and 0.88% methanol. A rhodium mirror and a layer of undissolved solids covered the immersed portion of the liner.

EXAMPLE III

Example I was repeated with the exception that 0.0217 gram (0.0833 mmole) of acridizinium bromide was used as the promoter and the mixture was kept under reaction conditions for 19 hours. A weight gain of 3.9690 grams was observed by measuring the liquid phase which by G.C. analysis was found to contain 7.84% ethylene glycol and 8.7% methanol along with small amounts of methyl formate and ethanol as well as 78.1% of tetraethylene glycol dimethyl ether. Analysis of the clear homogeneous liquid solution by atomic absorption methods revealed that 98% of the added rhodium was dissolved in the solution.

EXAMPLE IV

The following experiment was conducted using the equipment described in Example I. A suspension of rhodium(III) acetylacetonate (0.75 mmole), 2-hydroxypyridine (2.5 mmoles), 0.125 mmole of acridizinium bromide and 19.0 grams of tetraethylene glycol dimethyl ether solvent. This was placed in the autoclave, sealed and flushed with CO/H$_2$. Conditions were 8100 psig, CO/H$_2$ ratio 1:1, and 220° C. The recovered liquid reaction product was a clear greenish solution having 6.12% methanol and 3.91% ethylene glycol.

EXAMPLES V TO IX

A series of experiments described in Table 1 were completed with the conditions indicated. The results illustrate the variation in productivity and glycol to methanol ratio obtained when the ratio of rhodium to promoter is varied.

TABLE I

| EXAMPLE No. | RHODIUM CONC. | PROMOTER CONCENT. | Rh/Pr | ETHYLENE | CH$_3$OH % |
|---|---|---|---|---|---|
| EXAMPLE V | 0.00075M | 0.00138M | 2/1 | 4.61 | 8.95 |
| EXAMPLE VI | " | 0.00031M | 9/1 | 7.84 | 8.72 |
| EXAMPLE VII | " | 0.00062M | 4.5/1 | 5.10 | 7.60 |
| EXAMPLE VIII | " | 0.00028M | 10/1 | 2.93 | 4.13 |

Conditions:
Temp. 220° C.
Pressure — 8000 psig
CO/H$_2$ 1/1
Ligand — 2hydroxypyridine, 0.0091M
Solvent — tetraethylene glycol dimethyl ether

EXAMPLE X

A recycle experiment was conducted where the liquid product obtained as in Example III was submitted to a vacuum distillation (100 mmHg.) and a portion of the product, about 5 ml, collected as the overhead as the pot temperature was gradually increased to about 92° C. The overhead product was collected in a dry ice bath and g.c. analysis confirmed in all cases that the overhead contained the expected ethylene glycol, methanol and solvent. The bottoms from the partial disillation were diluted with fresh solvent and resubmitted to the original reaction conditions. The results of the four passes are shown in Table II.

| EXAMPLE No. | PASS No. | % ETHYLENE GLYCOL | % METHANOL |
|---|---|---|---|
| EXAMPLE X | 1 | 3.50 | 2.28 |
| EXAMPLE XA | 2 | 6.16 | 7.11 |
| EXAMPLE XB | 3 | 5.92 | 4.49 |
| EXAMPLE XC* | 4 | 1.49 | 1.18 |

*A rhodium mirror and a solid appeared in reaction product.
Conditions:
Temperature 220° C.
Pressure 8000 psig
CO/H$_2$ 1/1
Solvent — tetraethylene glycol dimethyl ether
Rh concentration 0.000275M
Promoter Conc. 0.00031M
Ligand 2-hydroxypyridine 0.00091M The results clearly show that the promoter (acridizinium bromide) can be recycled and maintains an acceptable glycol/methanol ratio during the process but does not prevent the ultimate conversion of the rhodium catalyst to an inactive form.

What is claimed is:

1. A process for preparing low molecular weight oxygenated products, especially ethylene glycol and methanol, from syngas which comprises contacting a mixture of carbon monoxide and hydrogen with a catalytic amount of a catalyst comprising a soluble rhodium-containing compound, an organic ligand and a cationic fused ring polynuclear aromatic compound possessing a nitrogen atom at a ring fusion position from the group consisting of salts of phenanthradaziniums, naphthaziniums, acridaziniums and derivatives thereof dissolved in a suitable solvent and heating the resulting mixture at a temperature of 150° C. to 350° C. and pressure of 1000 psig to 15,000 psig for sufficient time to produce the desired low molecular weight oxygenated products.

2. A process as in claim 1 wherein the rhodium-containing compound is selected from the group consisting of rhodium(III) chloride, rhodium sesquioxide, rhodium(III) acetylacetonate, rhodium dicarbonyl acetylacetonate, rhodium(III) acetate, rhodium(II) propionate and hexarhodium hexadecacarbonyl.

3. A process as in claim 1 wherein the ligand is an oxygen-containing ligand.

4. A process as in claim 1 wherein the ligand is a nitrogen-containing ligand.

5. A process as in claim 1 wherein the cationic polynuclear aromatic compound is acridizinium bromide.

6. A process as in claim 1 wherein the cationic polynuclear aromatic compound is acridizinium chloride.

7. A process as in claim 1 wherein the organic ligand is a Group VB tertiary donor ligand.

8. A process as in claim 1 wherein the solvent is an oxygenated hydrocarbon containing up to 12 carbon atoms.

9. A process as in claim 1 wherein the solvent is a dialkyl ether of a poly(alkylene glycol).

10. A process as in claim 1 wherein the process is conducted at a pressure of about 1000 psi to about 7500 psi.

11. A process as in claim 1 wherein the carbon monoxide and hydrogen are used in a ratio of 3:1 to 1:3.

12. A process as in claim 1 wherein the cationic aromatic compound is used in an amount varying from about 0.5 mol to 2.0 mol for every five atoms of rhodium present in the catalyst.

13. A process as in claim 1 wherein the rhodium-containing compound is rhodium(II) acetylacetonate.

14. A process as in claim 1 wherein the rhodium-containing compound is a rhodium oxide.

15. A process as in claim 1 wherein the rhodium-containing compound is rhodium diacetate.

16. A process as in claim 1 wherein the ligand is hydroxypyridine.

17. A process as in claim 1 wherein the polynuclear aromatic compound is a phenanthridizinium salt.

18. A process as in claim 1 wherein the polynuclear aromatic compound is a naphthazinium salt.

19. A process for preparing ethylene glycol from syngas which comprises contacting a mixture of carbon monoxide and hydrogen with a catalyst comprising a soluble rhodium-containing compound, an acridazinium salt, dissolved in a suitable solvent an organic ligand containing an element of the group consisting of oxygen, nitrogen, phosphorous, arsenic and antimony, and heating the resulting mixture at a temperature of 170° C. to 290° C. and a pressure of 1000 psig to 15,000 psig for sufficient time to produce the ethylene glycol, and then recovering the same from the reaction mixture.

* * * * *